(12) United States Patent
Guntzer et al.

(10) Patent No.: US 9,649,079 B1
(45) Date of Patent: May 16, 2017

(54) SYSTEM AND METHOD TO ILLUSTRATE A RADIATION DOSE APPLIED TO DIFFERENT ANATOMICAL STAGES OF AN EXPOSED SUBJECT

(71) Applicant: GENERAL ELECTRIC COMPANY, Schenectady, NY (US)

(72) Inventors: Pierre Guntzer, Strasbourg (FR); Philippe Roy, Strasbourg (FR); Luc Mertz, Strasbourg (FR)

(73) Assignee: General Electric Company, Schenectady, NY (US)

( * ) Notice: Subject to any disclaimer, the term of this patent is extended or adjusted under 35 U.S.C. 154(b) by 82 days.

(21) Appl. No.: 14/510,815

(22) Filed: Oct. 9, 2014

(51) Int. Cl.
*G06K 9/00* (2006.01)
*A61B 6/00* (2006.01)
*G06T 7/00* (2017.01)

(52) U.S. Cl.
CPC .............. *A61B 6/461* (2013.01); *A61B 6/488* (2013.01); *A61B 6/5217* (2013.01);
(Continued)

(58) Field of Classification Search
CPC ......... G06T 2207/30004; G06T 7/0012; G06T 2207/10081; G06T 2207/30061; G06T 7/20; G01T 1/02; G06K 2209/057
See application file for complete search history.

(56) References Cited

U.S. PATENT DOCUMENTS 5,635,709 A  6/1997  Sliski et al.
5,761,270 A  6/1998  Unfors
(Continued)

FOREIGN PATENT DOCUMENTS

EP  2072081 B1  3/2011
WO  9714017 A1  4/1997
(Continued)

OTHER PUBLICATIONS

Armato, III, Set al., "Automated Lung Segmentation for Thoracic CT", Academic Radiology, 7, 16 vol. 11, No. 9, Sep. 2004, 1011-1021, [online], [retrieved on Oct. 20, 2015]. Retrieved from the Internet: <URL:http://www.researchgate.net/profile/Samuel_Armato_III/publication/8362408_Automated_Lung_Segmentation_for_Thoracic_CT/links/54   75ea   7b0cf245eb4371168d.pdf?inViewer=true&pdfJsDownload=true&disableCoverPage=true&origin=publication_detail>; p. 1011, paragraph 1; Ref. Cite. No. 1, Armato et al., Automated lung segmentation for thoracic CT: Impact on computer-aided diagnosis, Academic Radiology, vol. 11, Issue 9, Sep. 2004, pp. 1011-1021, was properly considered.

*Primary Examiner* — Vu Le
*Assistant Examiner* — Guillermo Rivera-Martinez (57) ABSTRACT

A system and method to illustrate a radiation dose applied to different organs of an exposed subject with diagnostic image acquisition by an imaging scanner is provided. From a scout image, a computer processor can calculate a contour of an extremity of the exposed subject from the two-dimensional scout image; calculate a contour of a first organ dependent on a greyscale intensity of the plurality of pixels that comprise the two-dimensional scout image; calculate a contour of at least one anatomical stage dependent on a predefined geometric orientation relative the contour of the first organ; and apply a predefined auxology criteria to calculate a contour of a second organ dependent on a predefined geometric orientation relative to the contour of the at least one anatomical stage; and create a display illustrative of the a measurement of dose applied at the area defined by the contour of the anatomical stage.

16 Claims, 4 Drawing Sheets

(52) U.S. Cl.
CPC .. *G06T 7/0012* (2013.01); *G06T 2207/10116* (2013.01); *G06T 2207/30004* (2013.01)

(56) References Cited

U.S. PATENT DOCUMENTS

| | | | |
|---|---|---|---|
| 5,974,165 A * | 10/1999 | Giger | G06T 3/0075 |
| | | | 382/132 |
| 6,304,625 B1 | 10/2001 | Senzig | |
| 6,892,948 B2 | 5/2005 | Steklenski et al. | |
| 6,918,697 B2 | 7/2005 | Weidmann | |
| 7,227,152 B2 | 6/2007 | Brabec et al. | |
| 7,254,623 B1 | 8/2007 | Toth | |
| 7,313,223 B2 | 12/2007 | Unfors | |
| 7,399,977 B2 | 7/2008 | Rink et al. | |
| 7,432,510 B2 | 10/2008 | Yeo | |
| 7,441,955 B2 | 10/2008 | Guyonnet et al. | |
| 7,450,687 B2 | 11/2008 | Yeo et al. | |
| 7,627,079 B2 * | 12/2009 | Boone | G01T 1/2985 |
| | | | 378/210 |
| 7,652,268 B2 | 1/2010 | Patel | |
| 7,662,083 B2 | 2/2010 | Gueye et al. | |
| 7,801,273 B2 | 9/2010 | Hoornaert et al. | |
| 7,923,694 B2 | 4/2011 | Black et al. | |
| 8,107,589 B2 | 1/2012 | Sakurai et al. | |
| 8,119,978 B2 | 2/2012 | Islam et al. | |
| 8,133,167 B2 | 3/2012 | Gueye et al. | |
| 8,175,894 B2 | 5/2012 | Oowaki et al. | |
| 8,198,595 B2 | 6/2012 | Polishchuk | |
| 8,238,516 B2 | 8/2012 | Sakurai et al. | |
| 8,351,572 B1 | 1/2013 | Renner | |
| 8,412,544 B2 | 4/2013 | Reiner | |
| 2003/0098354 A1 | 5/2003 | Steklenski et al. | |
| 2004/0122308 A1 | 6/2004 | Ding | |
| 2004/0159803 A1 | 8/2004 | Akselrod et al. | |
| 2004/0227097 A1 | 11/2004 | Brabec et al. | |
| 2005/0061991 A1 | 3/2005 | Griggs et al. | |
| 2005/0209888 A1 | 9/2005 | Oowaki et al. | |
| 2006/0017009 A1 | 1/2006 | Rink et al. | |
| 2006/0056592 A1 | 3/2006 | Tamegai | |
| 2006/0153341 A1 | 7/2006 | Guyonnet et al. | |
| 2007/0071169 A1 | 3/2007 | Yeo et al. | |
| 2007/0114445 A1 | 5/2007 | Schell et al. | |
| 2007/0129593 A1 | 6/2007 | Gueye et al. | |
| 2007/0221864 A1 | 9/2007 | Neuhaus-Steinmetz et al. | |
| 2007/0241289 A1 | 10/2007 | Fung et al. | |
| 2008/0023647 A1 | 1/2008 | Patel | |
| 2008/0292055 A1 * | 11/2008 | Boone | G01T 1/02 |
| | | | 378/97 |
| 2009/0014665 A1 | 1/2009 | Fleming et al. | |
| 2009/0045352 A1 | 2/2009 | Morita | |
| 2009/0090865 A1 | 4/2009 | Lub et al. | |
| 2009/0161818 A1 | 6/2009 | Sakurai et al. | |
| 2009/0224176 A1 | 9/2009 | Patel | |
| 2010/0012829 A1 | 1/2010 | Islam et al. | |
| 2010/0099985 A1 | 4/2010 | Gueye et al. | |
| 2010/0104159 A1 | 4/2010 | Hirokawa et al. | |
| 2010/0239069 A1 | 9/2010 | Bourdeaux et al. | |
| 2011/0036988 A1 | 2/2011 | Campbell et al. | |
| 2011/0122400 A1 | 5/2011 | Ono et al. | |
| 2011/0260070 A1 | 10/2011 | Polishchuk | |
| 2012/0027273 A1 * | 2/2012 | Zankowski | G06T 7/0028 |
| | | | 382/128 |
| 2012/0080602 A1 | 4/2012 | Garcia et al. | |
| 2012/0106817 A1 | 5/2012 | Shih et al. | |
| 2012/0128116 A1 | 5/2012 | Sabol et al. | |
| 2012/0136194 A1 * | 5/2012 | Zhang | A61N 5/103 |
| | | | 600/1 |
| 2012/0148132 A1 | 6/2012 | Couch et al. | |
| 2012/0150505 A1 | 6/2012 | Couch et al. | |
| 2012/0150520 A1 | 6/2012 | Vaillant et al. | |
| 2012/0323108 A1 * | 12/2012 | Carroll | G06T 7/0014 |
| | | | 600/407 |
| 2013/0020508 A1 | 1/2013 | Kearfott | |
| 2013/0033700 A1 | 2/2013 | Hallil | |
| 2013/0064349 A1 | 3/2013 | Hyde et al. | |
| 2014/0148684 A1 | 5/2014 | Foo et al. | |

FOREIGN PATENT DOCUMENTS

| | | |
|---|---|---|
| WO | 9732630 A1 | 9/1997 |
| WO | 9852646 A1 | 11/1998 |
| WO | 2005119295 A1 | 12/2005 |
| WO | 2008006198 A1 | 1/2008 |
| WO | 2009111060 A3 | 12/2009 |
| WO | 2011137374 A1 | 11/2011 |
| WO | 2012071148 A1 | 5/2012 |
| WO | 2012075577 A1 | 6/2012 |
| WO | 2013034709 A1 | 3/2013 |
| WO | 2012051499 A3 | 4/2014 |

* cited by examiner

SYSTEM AND METHOD TO ILLUSTRATE A RADIATION DOSE APPLIED TO DIFFERENT ANATOMICAL STAGES OF AN EXPOSED SUBJECT

TECHNICAL FIELD

The subject matter described herein generally relates to a system and method to illustrate a measure of radiation dose applied to different anatomical stages of an exposed subject.

BACKGROUND

The statements in this section merely provide background information related to the disclosure and may not constitute prior art.

The subject matter of this application generally relates to ionizing radiation (e.g., x-rays), and more specifically to a system and method to measure ionizing radiation dose applied to various anatomical stages of an exposed subject.

Employment of the use of ionizing radiation (e.g., x-ray) is well known in the therapy or image acquisition of an exposed subject. Fields of application of ionizing radiation is common in the medical field (e.g., fluoroscopic, computed tomography (CT), x-ray, ablation of tissue, etc.) and security screening (e.g., airport baggage inspection). For example, radiological image acquisition generally includes directing a stream of ionizing radiation at the exposed subject, and measuring the attenuation of the ionizing radiation passing therethrough.

One concern with use of ionizing radiation includes an increased likelihood of harm or injury associated with radiation-induced injury to the tissue of the exposed subject. These deterministic risks can include skin reddening, rashes, burns, or hair loss. In fact, use of ionizing radiation is well-known in chemo-therapy or the ablation of diseased tissue. A variable that affects a likelihood of causing radiation-induced injury to tissue of an exposed subject includes a dose of radiation absorbed by the exposed subject. Variables that affect a dose of radiation absorbed by the exposed subject include a rate of delivery of radiation to the exposed subject, a time of exposure of radiation to the exposed subject, a fraction of radiation absorbed by the exposed subject, age or other characteristics of the exposed subject, and a location of exposure of radiation to the exposed subject. Another concern with use of ionizing radiation includes an increased likelihood of causing stochastic effects (e.g., radiation-induced cancers) to the exposed subject.

BRIEF SUMMARY

In view of the above concerns associated with use of ionizing radiation, there is a need for systems, methods and computer program products improved access to improve the knowledge to manage direction of radiation dose toward the exposed subject (e.g., patient) for different applications (e.g., fluoroscopic imaging, x-ray imaging, CT imaging of various exposed areas (e.g., chest, arms, legs, etc.) of an exposed subject). The above-described needs are addressed by the embodiments of the subject matter described herein.

One aspect of the subject matter includes a method of determination a radiation dose applied to different organs of an exposed subject with diagnostic image acquisition by an imaging scanner is provided. The method can include the steps of: acquiring a two-dimensional scout image associated with the exposed subject acquired with the imaging scanner; calculating with a computer processor a contour of an extremity of the exposed subject from the two-dimensional scout image; calculating a contour of a first organ dependent on a greyscale intensity of the plurality of pixels that comprise the two-dimensional scout image; calculating a contour of at least one anatomical stage dependent on a predefined geometric orientation relative the contour of the first organ; applying a predefined auxology criteria to calculate a contour of a second organ dependent on a predefined geometric orientation relative to the contour of the at least one anatomical stage; and creating a display illustrative of a measurement of dose applied at the area defined by the contour of the at least one anatomical stage.

According to another aspect, a system to illustrate a radiation dose applied to different organs of an exposed subject with diagnostic image acquisition by an imaging scanner is provided. From a two-dimensional scout image, a computer processor can calculate a contour of an extremity of the exposed subject; calculate a contour of a first organ dependent on a greyscale intensity of the plurality of pixels that comprise the two-dimensional scout image; calculate a contour of at least one anatomical stage dependent on a predefined geometric orientation relative the contour of the first organ; and apply a predefined auxology criteria to calculate a contour of a second organ dependent on a predefined geometric orientation relative to the contour of the at least one anatomical stage; and create a display illustrative of a measurement of dose applied at the area defined by the contour of the anatomical stage.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description in conjunction with the drawings in which reference numerals indicate identical or functionally similar elements.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. The term user and/or the plural form of this term are used to generally refer to those persons capable of accessing, using, or benefiting from the present disclosure. As used herein, when the phrase "at least" is used, it is open-ended in the same manner as the term "comprising" is open-ended.

Figure 1:
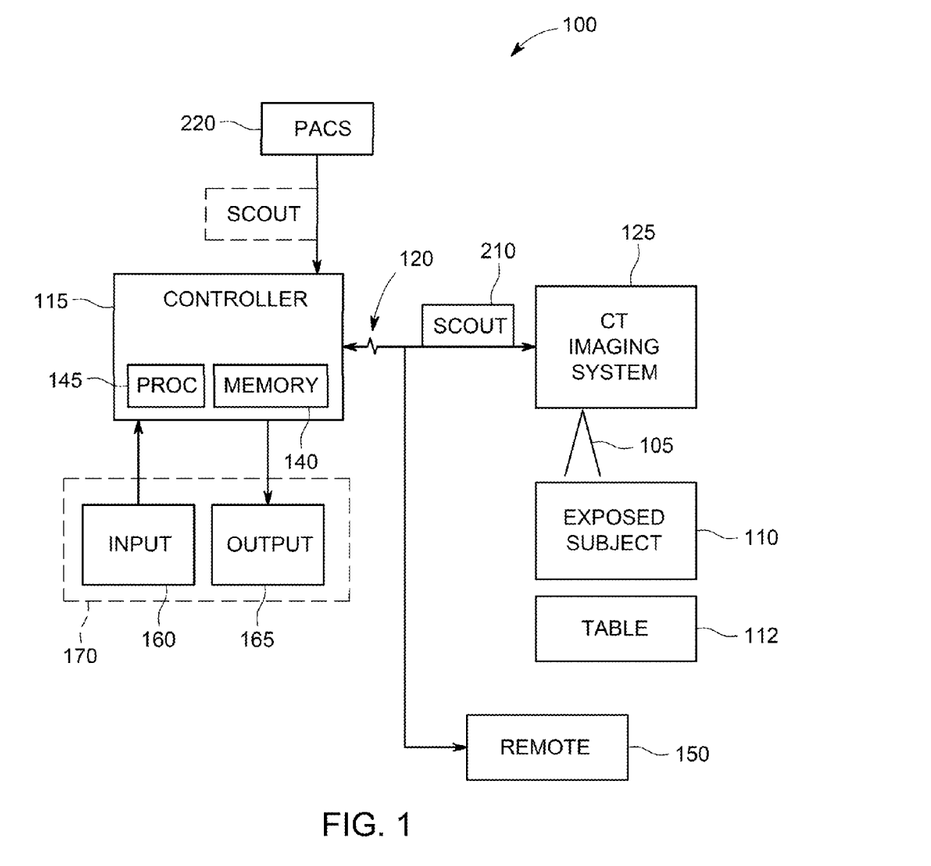
FIG. 1 shows a schematic block diagram of an example of a system in accordance to the subject matter described herein.

FIG. 1 illustrates one embodiment of a system 100 to track and report delivery of a radiation dose during or in an image acquisition procedure or other protocol involving direction of ionizing radiation 105 toward an exposed subject 110 supported on a table 112. The system 100 can generally include a controller 115 in communication via a network 120 with an image acquisition system 125 that employs ionizing radiation 105 in the generation of diagnostic images of the exposed subject 110 in accordance to the subject matter described herein. Although the controller 115 can be located remote from the image acquisition system 125, it should be understood that the controller 115 can otherwise be located integrated with or adjacent to the image acquisition system 125 and is not limiting on the subject matter described herein.

One example of the type of image acquisition system 125 can be an angiographic imaging system, computed tomography (CT), a fluoroscopic imaging system, etc. having the radiation source projecting the beam of ionizing radiation (e.g., x-rays) 105 toward the exposed subject 110 to be received at a detector in a conventional manner. The ionizing radiation 105 can be attenuated with passing through exposed subject 110, which the detector can translate the attenuation of ionizing radiation to generate the image data files (in electronic format) that can conventionally display or illustrate a region of interest of the exposed subject 110 in a known manner.

The controller 115 can generally include a memory 140 having a series of computer readable program instructions for execution by a computer or hardware processor (herein "computer processor") 145. The example memory 140 can include or be in the form of computer program product or medium of varying type generally operable to store electronic formatted data or information and program instructions accessible and readable by the computer processor 145. In certain examples, the memory 140 can be accessible by an external computing device (not shown) via the network 120. The computer-readable instructions can comprise a programming code for execution by the computer processor 145. The programming code can be embodied in software stored on the memory 140 independent of or in combination with software embodied in firmware or dedicated hardware.

The computer program product can include or be in the form of a computer-readable storage medium that is tangible, non-transitory, and having volatile and non-volatile, and removable and non-removable media for storage of electronic-formatted information such as computer readable program instructions or modules of instructions, data, etc. that may be stand-alone or as part of the controller 115. As used herein, the term tangible, non-transitory computer readable storage medium can be expressly defined to include any type of computer readable storage device and/or storage disk and to exclude propagating signal media and to exclude transmission media. As used herein, "non-transitory, tangible computer readable storage medium" and "non-transitory, tangible machine readable storage medium" can be used interchangeably.

Examples of the memory 140 can include, but are not limited to, random access memory (RAM), read only memory (ROM), Synchronous Dynamic Random Access Memory (SDRAM), Dynamic Random Access Memory (DRAM), EEPROM, flash memory, a cache, compact disc (CD), digital versatile disc (DVD) or other optical storage, magnetic cassettes, magnetic tape, magnetic disk storage or other magnetic storage devices, a hard drive, a flash memory, or any other medium which can be used to store the desired electronic format of information or program instructions for a duration and which can be accessed by the computer processor 145 or at least a portion of the controller 115.

The example computer processor 145 can include hardware operable to execute or perform one or more tasks as defined by the computer readable program instructions. The computer processor 145 can be, for example, part of a computer server, a laptop or desktop, a mobile device (e.g., a cell phone, a smart phone, a tablet such as an IPAD™), a personal digital assistant (PDA), an Internet appliance, or any other type of computing device. For example, the computer processor 145 can be implemented by one or more integrated circuits, logic circuits, microprocessors or controllers from any desired family or manufacturer.

The memory 140 and computer processor 145 as referred to herein can be stand-alone or integrally constructed as part of various programmable computing devices of various types, including for example a cache, a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like and any combination thereof operable to execute the instructions associated with implementing the method (discussed later) of the subject matter described herein.

The system 100 can be configured to communicate with miscellaneous remote computer devices 150 as referenced herein can include: a mobile telephone; a computer such as a desktop or laptop type; a Personal Digital Assistant (PDA) or mobile phone; a notebook, tablet or other mobile computing device; or the like and any combination thereof. The subject matter of this description may be implemented as the above-described stand-alone computer program product or for execution as an application capable of execution by one or more computing devices 150. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the remote computing device(s) 150.

The network 120 can facilitate transmission of electronic or digital data within and/or among the system 100. The example network 120 can be a wired interface (e.g., a data bus, a Universal Serial Bus (USB 2.0 or 3.0) connection, etc.) and/or a wireless interface (e.g., radio frequency, infrared, optical, near field communication (NFC), etc.), a wide area network (WAN); a local area network (LAN); the Internet; a cloud-based computing infrastructure of computers, routers, servers, gateways, etc.; or any combination thereof associated therewith that allows the system 100 or portion thereof to communicate with the image acquisition system 125 and various computing devices 150 described above. With respect to the example of the network 120 as including a cloud-based infrastructure, the system 100 can share information via web-based applications, cloud storage and cloud services. For example, a Web-based portal may be used to facilitate access to information, etc. The system 100 can illustrate the Web-based portal as a central interface to access information and applications, and data may be viewed through the Web-based portal or viewer, for example. Additionally, data may be manipulated and propagated using the Web-based portal, for example. The Web-based portal can be accessible locally (e.g., in an office) and/or remotely (e.g., via the Internet and/or other network or connection), for example.

The controller 115 can also be in communication with an input or input device 160 and an output or output device 165. Examples of the input device 165 include a keyboard, joystick, mouse device, touch-screen, pedal assemblies, track ball, light wand, voice control, or similar known input device known in the art. Examples of the output device 165 include a liquid-crystal monitor, a plasma screen, a cathode ray tube monitor, a touch-screen, a printer, audible devices, etc. The input device 160 and output device 165 can be integrated in combination with the image acquisition system 125, an independent of one another, or combination thereof as an interface 170 to the system 100.

Having provided an example of one construction of the system 100 as shown in FIG. 1 in accordance with above-description as well as various displays (see FIGS. 3-4) generated by the system 100, the following is a description of an example of a method 200 to operate the system 100 in determination of a radiation dose applied to specific organs of the exposed subject (e.g., patient) during the imaging procedure with the image acquisition system 125, in accordance with the subject matter described herein. It should also be understood that the sequence of the acts or steps of the method 200 as discussed in the foregoing description can vary. Also, it should be understood that the method 200 may not require each act or step in the foregoing description, or may include additional acts or steps not disclosed herein. It should also be understood that one or more of the steps of the method 200 can be represented by one or more computer program modules of computer-readable program instructions stored in the memory 140 of the system 100. As mentioned above, the method 200 can be implemented using coded instructions (e.g., computer and/or machine readable instructions). The terms module and component as referenced herein can generally represent program code or instructions that causes specified tasks when executed on the computer processor 145. The program code can be stored in one or more computer readable mediums that comprise the memory 140.

Figure 2:
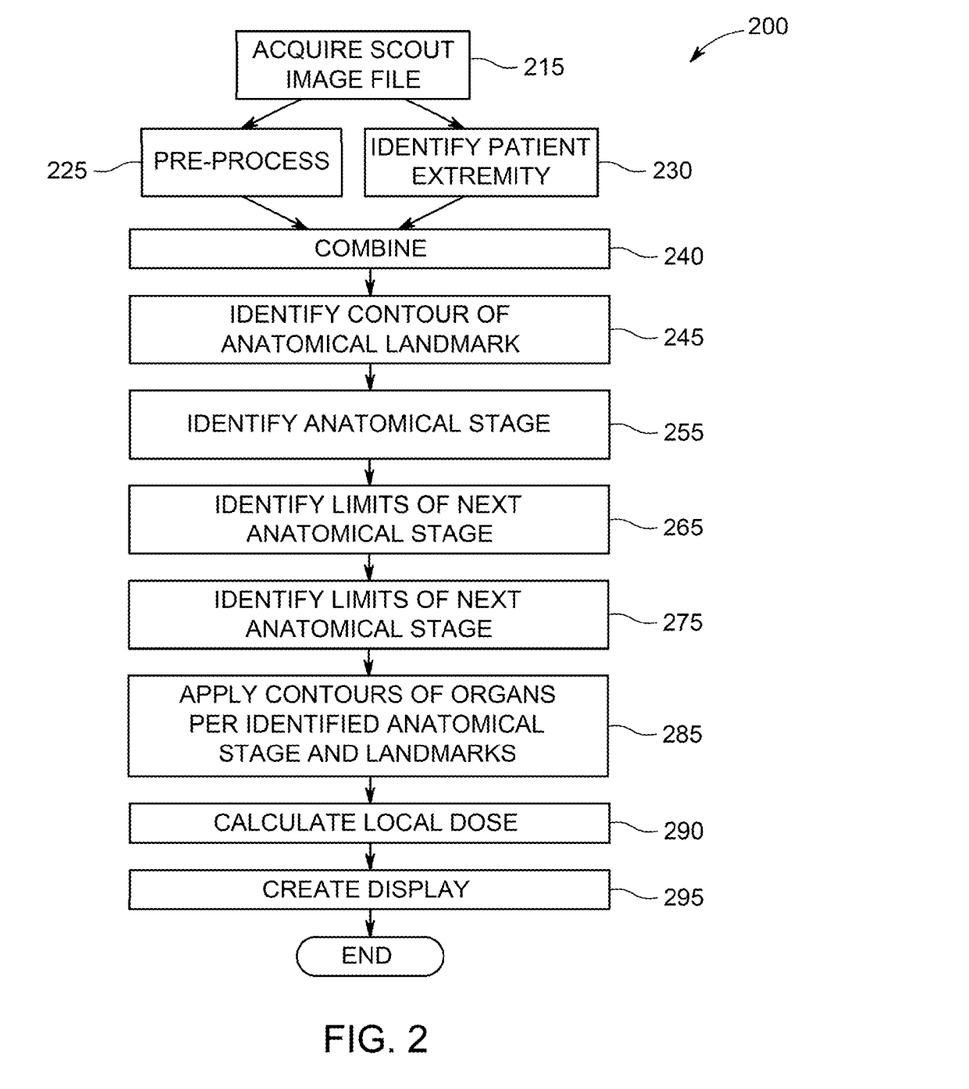
FIG. 2 shows a detailed illustration of a method of operation of the system of FIG. 1 in accordance with the subject matter described herein.

Assume the image acquisition system 125 has generated a DICOM AP scout image or image file (herein "scout image") 210, as well as has stored a scanning range associated with the DICOM AP scout image 210, for communication to the controller 115.

A DICOM image file can generally include a collection or series of tags (similar in concept to .xml or .html tags) where each tag includes a location of pixel data having a value that represents the pixel (i.e., basic unit of programmable color on a display monitor) associated with the tag. The remaining tags of a DICOM image file, other than the pixel data tags, can be referred to as metadata. The pixel data tags of the DICOM image file can include a DICOM scout or localizer image or image file (herein "scout image") in combination with a series of image slices. The scout image can be a two-dimensional DICOM instance or image of an orientation (e.g., defined by x and y axes) of haven been acquired along an X-axis (not shown) that corresponds to a horizontal axis extending in a direction from a left-hand border to a right-hand border of a surface of the table 112, and a Y-axis (not shown) that corresponds to a perpendicular axis to the X-axis in the horizontal plane extending from the lower limbs of the exposed subject 110 to his head. One example of an acquired image file includes a series that includes the scout image and the remaining images may be the "slices" or slice images (not shown) of patient image data as known in the art. This may be used for example, but not limited to, in CT and MR studies.

One example of the scout image can be a front planar view (e.g. a projection image of the exposed subject 110 resting on the table 112) of the relevant portion of interest of the exposed subject 110, while the slice images may be the cross-sectional diagnostic images of the exposed subject 110. The scout image can be a general illustration of the projected view of the exposed subject 110 different with respect to the slice images, the scout image generated to show a location of each of the acquired slice images relative to other acquired slices and their location with respect to the exposed subject 110. The illustration of the location of each of the slice images with respect to the scout image can be indicated by, for example, a graphic line (not shown) created for display in the scout image. From graphic illustration of the scout image, a user can select with a pointer, mouse or similar input selector device the particular graphic line (not shown) associated with one of the series of slice images for detailed viewing. The illustration of the graphic line in the scout image can change positions to reflect a position of the slice of current interest for detailed viewing. As well understood to one skilled in the art, each of slice images are generally similar in diagnostic image data content to other slice images associated with the exposed subject 110, while the scout image is generally very different viewpoint of the exposed subject 110 and lower image resolution relative to the series of slice images.

Step 215 includes the system 100 receiving the scout image file and scanning range received from the image acquisition system 125 or from an alternative image file source (e.g., picture archival system (PACS)) 220.

Step 225 can include performing pre-processing on the scout image file. An example of step 225 can include applying convolution filters to the scout image file 210. Examples of convolution filters include median or Gaussian blur filters known to those skilled in the art. Step 225 includes calculating a contour 230 of an extremity (i.e., exterior or skin surface) of the exposed subject 110 from the scout image file 210 acquired by the system 100.

The system 100 can calculate the contour 230 of the extremity dependent on image processing with the computer processor, such as comparing or analyzing a greyscale intensity of the candidate pixels comprising the scout image file 210 to define the contour 230. Image processing can further include analysis or comparison of a geometric location of the candidate pixels relative to predefined reference. Based on this above-described analysis, the system 100 can calculate with the computer processor 145 a score for each of the candidate pixels to define the contour 230 of the extremity. Dependent on a comparison of the scores of the candidate pixels to one another, the computer processor 145 can identify and enhance display of the subset of candidate pixels (e.g., create overlying a new line, increase width of candidate pixels, increase greyscale intensity, or combination thereof) to further differentiate illustration of the contour 230 of the extremity from other pixels that comprise the acquired scout image file 210.

Step 240 can include creating a combined image file that includes combining the pre-processed scout image file and the calculated exposed subject contour of the extremity 230 of the exposed subject 110 as described above. Step 245 can include performing image processing of the combined image file to detect and delineate a contour 250 that defines a first anatomical landmark or limit of the exposed subject 110. In this example, the contour 250 of the first anatomical landmark or limit can be located at an intersection of the shoulder and the head of the exposed subject. The delineation of the contour 250 can be detected based on image processing directed to identifying pixels of greyscale intensity and width associated with a high increase in exposed subject thickness.

Figure 3:
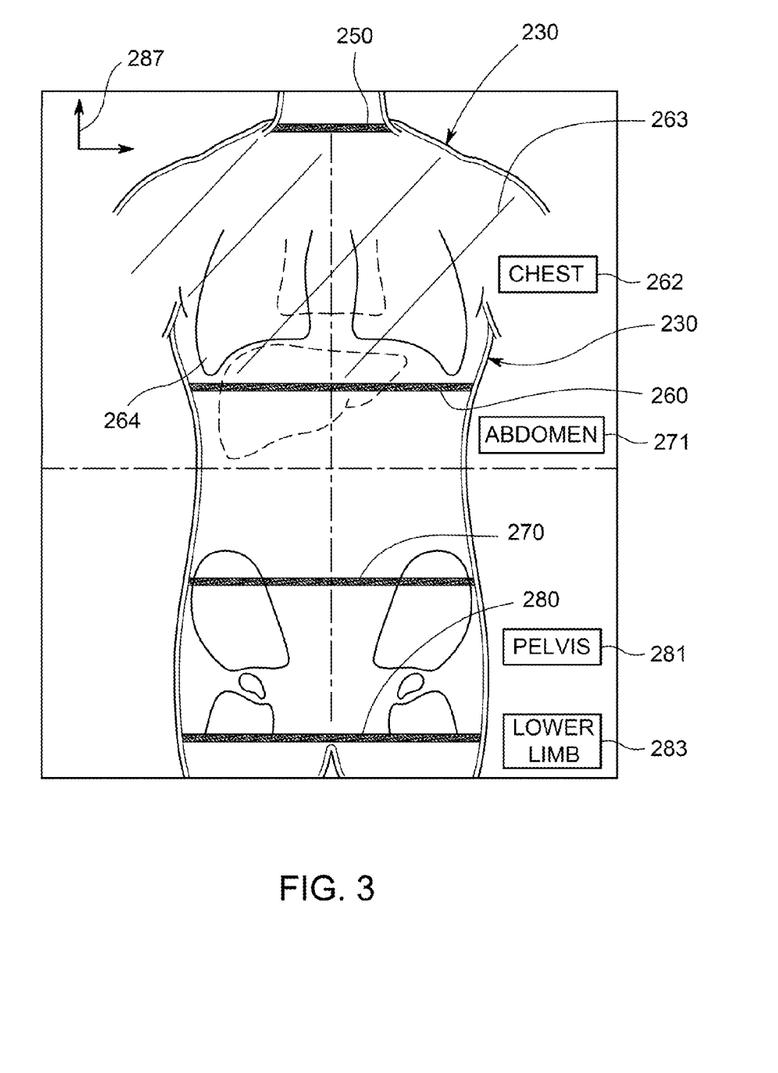
FIG. 3 shows a detailed schematic illustration of a display generated by the system of FIG. 1 in accordance with the subject matter described herein.

Step 255 can include calculating a contour 260 that generally defines a lower limit of a first predefined anatomical stage. Referring to FIG. 3, an anatomical stage (See for example chest anatomical stage 262 of region delineated by cross-hatch lines 263) can be defined as a region of interest of the exposed subject 110 at least defined on two sides by the contour 230 of the extremity of the exposed subject 110, and in the other two sides (i.e., in a head to toe direction of the exposed subject 110) by anatomical landmarks or limits as described herein. In one example of executing a first analysis of the shape of the contour 260 of lower limit of the chest anatomical stage, the system 100 can calculate if the scout image 210 illustrates image data above the anatomical stage 262 of the chest region, including the chest region, or below chest region. According to one embodiment, the system 100 detects the series of anatomical stages of the exposed subject 110 according to the following sequential order: head (not shown), then chest (see reference 262), then abdomen (see reference 271), then pelvis (see reference 281). If a first limit is not found, the system 100 may try to find other in a list of limits in a direction of head of toe of the exposed subject 110, dependent on a predefined geometric orientation relative the identified contours 230 and 250 described above. In this example, the contour 260 of the lower limit of the anatomical stage 262 of the chest region can be defined by identification of candidate pixels that illustrate lower limit of an organ such as a lung (see reference 264), or a predefined distance based on stored data of auxology therefrom.

This step 255 of calculating contour 260 can include performing image processing to detect and identify best candidate pixels defining the combined image file that correspond to the boundary or contour of the lungs 264. According to one embodiment, step 255 can include applying an algorithm (e.g., calculating a normalized correlation coefficient) to identify and delineate pixels in the combined image file that are best candidates to correspond to image data of one or both right and left lungs 264. Step 255 can also include applying geometric criteria associated with stored auxology information to perform a benchmark comparison of the candidate pixels defining the contour of the lung 264 as it defines the contour of the anatomical stage 262.

Although the step of calculating the contour 260 of the lower limit of the first anatomical stage is described above with respect to the anatomical stage 262 of the chest region, it should be understood that the first anatomical stage can vary. In another example, the system 100 can calculate the contour 260 of the anatomical stage of the head as defining the imaged area between a top of the exposed subject 110 and the contour 250 of the first anatomical landmark where the neck meets the shoulders.

Step 265 includes calculating a contour 270 that defines the limits of another anatomical stage of the exposed subject 110. In this next example, the anatomical stage 271 is the abdomen region, located just below the anatomical stage 262 for the chest region. Assume that the contour 260 that defines the lower limit of the anatomical stage 262 for the chest region, and the contour 230 defines the external boundary of the exposed subject 110. The remaining boundary of the anatomical stage 271 for the abdomen is then defined by the contour 270. In calculating the contour 270, step 265 can include applying predefined auxology criteria to calculate the contour 270 of the second anatomical stage dependent on a predefined geometric orientation relative to the contour 260 of the first anatomical stage. For example where the first anatomical stage is the chest region and another or subsequent anatomical stage to calculate is of an abdomen region, the step 265 of applying the predefined auxology criteria to calculate the lower limit or contour 270 of the abdomen region can include estimating a dimension of the abdomen region dependent on the contour 230 of the extremity of the exposed subject 110, heuristic data (e.g., age, sex, weight, etc. minimum and maximum ratio between chest width and abdomen height for human body, minimum distance between most left point of iliac bone and most left point of the contour normalized with patient thickness . . . ) that benchmarks the limits of the anatomical stage for the abdomen region relative to the lower limit or contour 260 of the anatomical stage for the chest region, etc.

Step 275 can include applying heuristic and auxology criteria to detect and identify a contour 280 of the region of pixel data that correlate or define a limit of an anatomical stage 281 of pelvis region or zone. Step 275 can include generating a plot profile of the pixel data along a z-axis and identifying a candidate contour best corresponding to an upper limit of the anatomical stage 281 of the pelvis region, characterized by a high peak in the image data located close to the exposed subject outer contour 230 that decreases rapidly and a peak in the image data located toward a middle point between the exposed subject contours 230 that corresponds to a spinal region of the exposed subject 110. The system 100 can execute multiple techniques to calculate a score in characterizing candidate contours, including detecting symmetric properties of candidate contours or pixels of an anatomical region (e.g., along the spine), detecting peaks of a candidate contours included in a convolution image, and selecting best candidate contours based on their orientation and relative adjacency.

In one example, step 275 can include generating a plot profile of the pixel data along a z-axis and identifying a candidate contour best corresponding to a lower limit 280 of the pelvis region, characterized by a high peak in the image data located nearest to the exposed subject outer contour that decreases rapidly and a peak in the image data located toward a middle between the exposed subject contours that corresponds to an upper limit of the lower limbs of the exposed subject 110.

In another example, step 255 in defining the contour of the anatomical stage for the abdomen region can include defining an upper limit or contour 260 of the anatomical stage 271 for the abdomen region as the lower limit of the anatomical stage for the chest region, and defining the lower limit or contour 270 of the anatomical stage 271 for the abdomen region as the upper limit or contour 270 of the anatomical stage 281 for the pelvis region.

The steps 255 or 275 can be implemented to calculate an anatomical stage 283 for the lower limb region too. The contour 280 (i.e., the lower limit or contour of the anatomical stage for the pelvis region) calculated above can be applied to define the upper limit of the anatomical stage 283 for the lower limbs. The contours 230 of the lowest limits or extremities of the exposed subject 110 can define the remaining contours or limits or boundaries that define the anatomical stage 283 for the lower limb region of the exposed subject 110.

Step 285 can include defining coordinates relative to a frame or coordinate system 287 that defines the combined image file that correlate to contours, limits or boundaries of predefined anatomical structures based on stored or predefined auxology and geometric criteria relative to the limits of the anatomical stages identified above.

Step 290 can include calculating an applied, local dose of radiation for the anatomical stage. An example of the step 290 of calculating the local dose of radiation can be computed relative to the coordinates or limits in a two-dimensional plane that defines the anatomical stages described above. For example, a local dose or dose length product (DLP) for the anatomical stage can be computed by a summation of a height (H1) of an intersection between a radiation emission of this series and an anatomical stage and a height (H2) of a corresponding radiation emission of this series, reflected by the following:

Anatomical Stage DLP=Σ[Local DLP×(H1/H2)]

Upon mapping the applied, local dose to the combined image file in step 290, step 295 can include the system 100 creating a combined graphic display illustrative of the local radiation dose applied in combination with and relative to the contours or limits of the anatomical stages of the exposed subject 110 described above.

Figure 4:
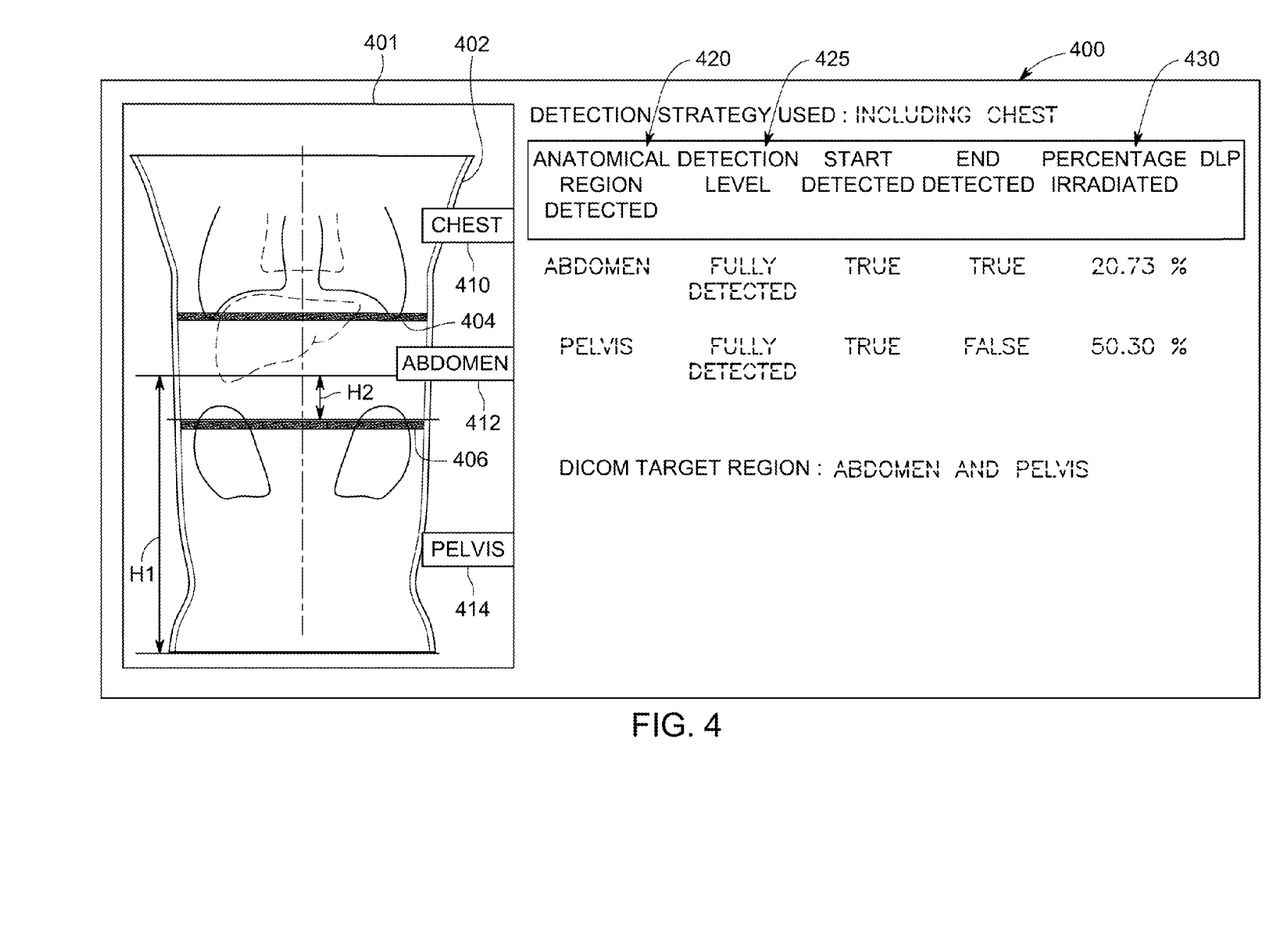
FIG. 4 shows a detailed schematic illustration of another display generated by the system of FIG. 1 in accordance with the subject matter described herein.

FIG. 4 illustrates an example of a display 400 (e.g., user interface illustration) that visually illustrates the output from the system 100 and method 200 of operation described above. The display 400 includes an illustration 401 of the contours or limits 402, 404, and 406 that define the boundaries of the predefined anatomical stages 410, 412, 414, respectively, similar to the contours 230, 260, and 270 that define the stages 262, 271, and 281 described above and shown in FIG. 3. The display 400 can further include a graphic illustration 420 describing the anatomical stage detected, a graphic illustration 425 of the detection level of the anatomical stage, and a graphic illustration 430 of the value of the measure (e.g., percentage total) of irradiation applied at each anatomical stage. The illustrated graphic illustrations can be shown independently in a table format or in combination with the graphic illustrations of the contours defining the anatomical stages.

Technical effects of the subject matter described above can include, but is not limited to, providing the system 100 and method 200 to calculate the split or differentiation of estimated applied, local dose to different, predefined anatomical stages of the exposed subject 110. Thereby, the system 100 and method 200 accomplish dose mapping based on acquired image data from the scout image file 210, without the need for other information about the protocol used in the imaging procedure, radiological information system (RIS), etc. that may not be available or reliably accurate for the actual procedure performed.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of determination a radiation dose applied to different anatomical stages of an exposed subject with diagnostic image acquisition by an image acquisition system, the method comprising the steps of:

acquiring a two-dimensional frontal planar view scout image associated with the exposed subject acquired with the image acquisition system;

calculating with a computer processor a contour of an extremity of the exposed subject from the two-dimensional frontal planar view scout image;

calculating a contour of a first organ dependent on a greyscale intensity of the plurality of pixels that comprise the two-dimensional frontal planar view scout image;

calculating a contour of at least one anatomical stage dependent on a predefined geometric orientation relative to the contour of the first organ;

applying a predefined auxology criteria to calculate a contour of a second organ dependent on a predefined geometric orientation relative to the contour of the at least one anatomical stage; and create a display illustrative of a measurement of dose applied at the area defined by the contour of the at least one anatomical stage.

2. The method of claim 1, further including the step of:
calculating a local dose of radiation applied within the contour of the at least one anatomical stage of the exposed subject.

3. The method of claim 2, further including the step of:
creating a graphic display illustrative of the local radiation dose applied relative to the contour of the at least one anatomical stage of the exposed subject.

4. The method of claim 1, wherein the step of calculating the contour of the first organ includes the steps of:

analyzing with the computer processor a greyscale intensity and a geometric location for each of the plurality of pixels with the scout image, the geometric location relative to a reference;

calculating with the computer processor a score for each of the plurality of pixels dependent on the greyscale intensity and the geometric location of each of the plurality of pixels.

5. The method of claim 4, further including the step of:
calculating with the computer processor a subset of candidate pixels that define a predefined contour of the first organ of the exposed subject dependent on the score for each of the plurality of pixels; and calculating with the computer processor, dependent on a comparison of the scores of the subset of candidate pixels to one another, the contour of the at least one anatomical stage of the exposed subject dependent on the predefined orientation of the contour of the first organ.

6. The method of claim 1, wherein the at least one anatomical stage includes one of a head, a neck, a thorax, an abdomen, a pelvic region and a lower member of the exposed subject.

7. The method of claim 6, wherein the first organ is a lung, and the contour of the thorax is defined by the contour of the lung.

8. The method of claim 1, wherein the first organ is a lung and the at least one anatomical stage is an abdomen, and the step of applying a predefined auxology criteria to calculate the contour of the second organ includes estimating a contour of an abdomen dependent on the contour of the extremity of the exposed subject and a predefined dimension of the lung.

9. A system to illustrate a radiation dose applied to different organs of a exposed subject with diagnostic image acquisition by an imaging scanner, comprising:
    acquiring a two-dimensional frontal planar view scout image associated with the exposed subject acquired with the imaging scanner;
    calculating with a computer processor a contour of an extremity of the exposed subject from the two-dimensional frontal planar view scout image;
    calculating a contour of a first organ dependent on a greyscale intensity of the plurality of pixels that comprise the two-dimensional frontal planar view scout image;
    calculating a contour of at least one anatomical stage dependent on a predefined geometric orientation relative the contour of the first organ;
    applying a predefined auxology criteria to calculate a contour of a second organ dependent on a predefined geometric orientation relative to the contour of the at least one anatomical stage;
    creating a graphic display illustrative of the contour of the at least one anatomical stage.

10. The system of claim 9, calculating a local dose of radiation applied within the contour of the at least one anatomical stage of the exposed subject.

11. The system of claim 10, further including the step of:
    creating a graphic display illustrative of the local radiation dose applied relative to the contour of the at least one anatomical stage of the exposed subject.

12. The system of claim 9, wherein the step of calculating the contour of the first organ includes the steps of:
    analyzing with the computer processor a greyscale intensity and a geometric location for each of the plurality of pixels with the scout image, the geometric location relative to a reference;
    calculating with the computer processor a score for each of the plurality of pixels dependent on the greyscale intensity and the geometric location of each of the plurality of pixels.

13. The system of claim 12, further including the step of:
    calculating with the computer processor a subset of candidate pixels that define a predefined contour of the first organ of the exposed subject dependent on the score for each of the plurality of pixels; and
    calculating with the computer processor, dependent on a comparison of the scores of the subset of candidate pixels to one another, the contour of the at least one anatomical stage of the exposed subject dependent on the predefined orientation of the contour of the first organ.

14. The system of claim 9, wherein the at least one anatomical stage includes one of a head, a neck, a thorax, an abdomen, a pelvic region and a lower member of the exposed subject.

15. The system of claim 14, wherein the first organ is a lung, and the contour of the thorax is defined by the contour of the lung.

16. The system of claim 9, wherein the first organ is a lung and the at least one anatomical stage is an abdomen, and the step of applying a predefined auxology criteria to calculate the contour of the second organ includes estimating a contour of an abdomen dependent on the contour of the extremity of the exposed subject and a predefined dimension of the lung.

* * * * *